US010070965B2

(12) United States Patent
Hagen et al.

(10) Patent No.: US 10,070,965 B2
(45) Date of Patent: Sep. 11, 2018

(54) KNEE JOINT ENDOPROSTHESIS

(71) Applicant: Aesculap AG, Tuttlingen (DE)

(72) Inventors: Thomas Hagen, Tuttlingen (DE);
Roland Boettiger, Rietheim-Weilheim (DE); Michael Willmann, Villingen-Schwenningen (DE); Harry Kempf, Stetten a. k. M. (DE)

(73) Assignee: Aesculap AG, Tuttlingen (DE)

( * ) Notice: Subject to any disclaimer, the term of this patent is extended or adjusted under 35 U.S.C. 154(b) by 0 days.

(21) Appl. No.: 15/290,466

(22) Filed: Oct. 11, 2016

(65) Prior Publication Data

US 2017/0027706 A1    Feb. 2, 2017

Related U.S. Application Data

(63) Continuation of application No. PCT/EP2015/059321, filed on Apr. 29, 2015.

(30) Foreign Application Priority Data

Apr. 29, 2014  (DE) .................. 10 2014 106 012

(51) Int. Cl.
*A61F 2/38* (2006.01)
*A61F 2/30* (2006.01)

(52) U.S. Cl.
CPC ............ *A61F 2/3845* (2013.01); *A61F 2/384* (2013.01); *A61F 2/385* (2013.01); *A61F 2/3836* (2013.01); *A61F 2002/3049* (2013.01); *A61F 2310/00005* (2013.01)

(58) Field of Classification Search
CPC .......... A61F 2/38; A61F 2/384; A61F 2/3836
See application file for complete search history.

(56) References Cited

U.S. PATENT DOCUMENTS

| 4,209,861 A | 7/1980 | Walker et al. |
| 4,340,978 A | 7/1982 | Buechel et al. |
| 5,755,804 A | 5/1998 | Schmotzer et al. |

(Continued)

FOREIGN PATENT DOCUMENTS

| CN | 101627930 | 1/2010 |
| CN | 102076283 | 5/2011 |

(Continued)

OTHER PUBLICATIONS

International Search Report for corresponding application No. PCT/EP2015/059321, dated Jul. 27, 2015, 2 pages.

*Primary Examiner* — Bruce E Snow
(74) *Attorney, Agent, or Firm* — Lipsitz & McAllister, LLC (57) ABSTRACT

The invention relates to a knee joint endoprosthesis has a tibia part, a femur part, a meniscus part arranged on the tibia part in mutually non-rotatable manner and a connecting device for connecting the tibia part to the femur part in articulated manner. Said femur part comprises at least one femur condyle having a femur condyle surface. Said meniscus part comprises at least one upper surface which faces the femur part and has at least one meniscus joint surface which touches the femur condyle surface of the at least one femur condyle. Said femur part and the tibia part are mounted such as to be rotatable relative to each other about a rotational axis.

20 Claims, 8 Drawing Sheets

(56) References Cited

U.S. PATENT DOCUMENTS

| | | | |
|---|---|---|---|
| 5,964,808 A | 10/1999 | Blaha et al. | |
| 2004/0186583 A1 | 9/2004 | Keller | |
| 2005/0107886 A1* | 5/2005 | Crabtree | ................ A61F 2/385 |
| | | | 623/20.24 |

FOREIGN PATENT DOCUMENTS

| | | |
|---|---|---|
| CN | 102596108 | 7/2012 |
| CN | 103153237 | 6/2013 |
| DE | 2122390 | 1/1973 |
| DE | 2906458 | 1/1984 |
| DE | 4102509 | 6/1996 |
| DE | 69206397 | 8/1996 |
| DE | 69323077 | 6/1999 |
| DE | 69324016 | 10/1999 |
| DE | 102009007724 | 8/2010 |
| EP | 0923916 | 6/1999 |
| EP | 1226800 | 7/2002 |
| EP | 1132064 | 2/2007 |
| EP | 2213262 | 8/2010 |

\* cited by examiner

KNEE JOINT ENDOPROSTHESIS

CROSS-REFERENCE TO RELATED APPLICATIONS

This application is a continuation of international application number PCT/EP2015/059321 filed on Apr. 29, 2015 and claims the benefit of German application number 10 2014 106 012.1 filed on Apr. 29, 2014, which are incorporated herein by reference in their entirety and for all purposes.

FIELD OF THE INVENTION

The present invention relates to knee joint endoprostheses generally, and more specifically to a knee joint endoprosthesis having a tibia part, a femur part, a meniscus part arranged on the tibia part in mutually non-rotatable manner and a connecting device for connecting the tibia part to the femur part in articulated manner, wherein said femur part comprises at least one femur condyle having a femur condyle surface, wherein said meniscus part comprises at least one upper surface which faces the femur part and has at least one meniscus joint surface which touches the femur condyle surface of the at least one femur condyle.

BACKGROUND OF THE INVENTION

Knee joint endoprostheses of the type described hereinabove are known from DE 2 122 390 A for example. This relates in particular to so-called hinge joint knee prostheses in which the connecting device comprises a hinge joint in order to enable flexion between the lower leg and the thigh to be effected in a similar way to that of the natural knee joint.

However, the kinematics of the natural knee joint are far more complicated than a simple hinge joint. The consequence of this being that patients having implanted knee joint endoprostheses of the type described complain about restricted mobility.

SUMMARY OF THE INVENTION

In a first aspect of the invention a knee joint endoprosthesis has a tibia part, a femur part, a meniscus part arranged on the tibia part in mutually non-rotatable manner and a connecting device for connecting the tibia part to the femur part in articulated manner. Said femur part comprises at least one femur condyle having a femur condyle surface. Said meniscus part comprises at least one upper surface which faces the femur part and has at least one meniscus joint surface which touches the femur condyle surface of the at least one femur condyle. Said femur part and the tibia part are mounted such as to be rotatable relative to each other about a rotational axis. Said femur condyle surface of the at least one femur condyle and the at least one meniscus joint surface are formed in correspondence with one another in such a manner that the femur condyle surface of the at least one femur condyle defines a section of a spherical surface or substantially a section of a spherical surface. And said at least one meniscus joint surface is formed as a joint surface recess in the form of a curved hollow which is matched to the femur condyle surface.

BRIEF DESCRIPTION OF THE DRAWINGS

The foregoing summary and the following description may be better understood in conjunction with the drawing figures, of which.

DETAILED DESCRIPTION

Although the invention is illustrated and described herein with reference to specific embodiments, the invention is not intended to be limited to the details shown. Rather, various modifications may be made in the details within the scope and range of equivalents of the claims and without departing from the invention.

The present invention relates to a knee joint endoprosthesis having a tibia part, a femur part, a meniscus part arranged on the tibia part in mutually non-rotatable manner and a connecting device for connecting the tibia part to the femur part in articulated manner, which femur part comprises at least one femur condyle having a femur condyle surface, which meniscus part comprises at least one upper surface which faces the femur part and has at least one meniscus joint surface which touches the femur condyle surface of the at least one femur condyle, wherein the femur part and the tibia part are mounted such as to be rotatable relative to each other about a rotational axis, wherein the femur condyle surface of the at least one femur condyle and the at least one meniscus joint surface are formed in correspondence with one another in such a manner that the femur condyle surface of the at least one femur condyle defines a section of a spherical surface or substantially a section of a spherical surface and wherein the at least one meniscus joint surface is formed as a joint surface recess in the form of a curved hollow which is matched to the femur condyle surface.

In the case of such a knee joint endoprosthesis, it is possible, in particular, for the tibia part and the femur part to not only swivel relative to each other about a hinge axis but also to rotate about a rotational axis. For example, the rotational axis may correspond substantially to a longitudinal axis of the tibia of the patient. Thus, at the same time as a flexion of the knee, a more or less highly pronounced rotation about a longitudinal axis of the leg of the patient can also take place. In order to minimize a susceptibility for wear of the knee joint endoprosthesis and in particular of the meniscus part thereof, it is advantageous to construct the at least one femur condyle and the at least one meniscus joint surface in the manner described. Thus, in particular, a linear contact can be ensured independently of a flexional or a rotational position of the tibia part and the femur part relative to each other.

Overall therefore, a particularly large degree of congruence between the meniscus part fixed to the tibia part and the femur part can be achieved. In addition, the joint surface recess that is preferably curved convexly away from the rotational axis can extend over a given angular rotational range. In particular, the angular rotational range can be predetermined in dependence on the patient in order to permit a limited rotation of the femur part and the tibia part relative to each other about the rotational axis. Thus for example, provision can be made for a rotation within a range of ±20° or even of ±12°. The curved joint surface recess then preferably has an arc length which corresponds to the desired angular rotational range. A cross section of the hollow transverse to its curvature can, in particular, be circular or even elliptical. The meniscus part can, in particular, be safeguarded from rotation with the tibia part by means of an anti-twist arrangement. Alternatively or additionally, snap-action, screw-action or some other form of connecting mechanism could also be provided in order to fix the meniscus part to the tibia part in mutually non-rotatable manner or completely immovable manner.

It is expedient for the femur part to comprise a medial and a lateral femur condyle which define a medial femur condyle surface and a lateral femur condyle surface, for the meniscus part to comprise a medial and a lateral meniscus joint surface, for the medial femur condyle surface to touch the medial meniscus joint surface and for the lateral femur condyle surface to touch the lateral meniscus joint surface. It is then possible, in particular, for a femur part to be equipped in the described manner with two femur condyles so that two contact zones or contact regions are defined between the femur part and the meniscus part. The design of the two femur condyle surfaces in the form of sections of spherical surfaces makes it possible, in particular, for at least one linear contact between the femur part and the meniscus part to be obtained on both the lateral side and the medial side.

Preferably, the medial femur condyle surface and the lateral femur condyle surface have an identical or substantially identical femur condyle radius of curvature. It is thereby possible, in particular, to construct the femur condyles such that they are substantially symmetrical with respect to a plane of symmetry containing the rotational axis. In corresponding manner, the meniscus part can also be formed so as to be symmetrical with respect to a plane of symmetry containing the rotational axis. This simplifies not only the construction of the meniscus part but also the production thereof.

It is advantageous furthermore, if the medial femur condyle surface and the lateral femur condyle surface have femur condyle radii of curvature which differ from each other. In particular, this permits the femur condyles on the femur part to be constructed in differing sizes. Thus in particular, a femur part which comes particularly close to a natural femur can then be produced. For example, that femur condyle surface which is most heavily loaded by the movement of the knee can be formed with a larger femur condyle radius of curvature in order to achieve as large a contact between the femur part and the meniscus part as possible whereby in particular, wear and in particular wear of the meniscus part can be minimized.

It is expedient furthermore, if the medial meniscus joint surface and the lateral meniscus joint surface have an identical or substantially identical meniscus joint surface radius of curvature. Such an arrangement is then advantageous in particular when the medial and lateral femur condyle surfaces also have an identical or substantially identical femur condyle radius of curvature. Consequently, a linear or substantially linear contact can be achieved on both the medial side and the lateral-side, namely, in dependence on a flexional and/or a rotational angle between the femur part and the tibia part.

Furthermore, it can be advantageous if the medial meniscus joint surface and the lateral meniscus joint surface have meniscus joint surface radii of curvature which differ from each other. In particular, the meniscus joint surface radii of curvature can be defined as radii of curvature of lines of intersection of the meniscus part with a cutting plane containing the rotational axis. The meniscus joint surfaces are preferably curved concavely away from the meniscus part due to the correspondence between the construction thereof and that of the femur condyle surfaces.

Preferably, the at least one meniscus joint surface is formed concentrically or substantially concentrically with respect to the rotational axis. Thus in particular, the joint surface recess can be in the form of a curved hollow which is concentric with the rotational axis. In this way, the at least one femur condyle can be guided in the hollow meniscus joint surface when there is a rotation of the femur part relative to the tibia part. Consequently, and in particular independently of a flexional and a rotational position of the femur part and the tibia part relative to each other, an optimal contact such as an at least linear contact for example of the femur condyle surface of the at least one femur condyle on the at least one meniscus joint surface can be achieved.

In accordance with a further preferred embodiment of the invention, provision may be made for the at least one meniscus joint surface to be concavely curved in a direction pointing away from the meniscus part and to have a meniscus joint surface radius of curvature in an arbitrary cutting plane containing the rotational axis which corresponds or substantially corresponds to a femur condyle radius of curvature of the femur condyle surface of the at least one femur condyle which is convexly curved in a direction pointing away from the femur part. In particular in the case of conformity of the meniscus joint surface radius of curvature and the femur condyle radius of curvature, a linear contact of the femur part on the meniscus part can then be ensured in particular independently of a rotational and/or flexional position of the femur part and the tibia part relative to each other.

Preferably, the meniscus joint surface radii of curvature of arbitrary cutting planes containing the rotational axis are identical or substantially identical. Thus in particular, a linear contact of the femur part on the meniscus part can be achieved independently of a rotational position. Alternatively, the radii of curvature could also increase or decrease in dependence on a rotational angular position between the femur part and the tibia part. Furthermore, a curvature of the meniscus joint surface could also change in a cutting plane. Thus for example, a line of intersection of the meniscus part with the cutting plane does not necessarily have to be in the form of a section of a circular arc, but alternatively, could also be a section of an ellipse.

In order to enable the knee joint endoprosthesis to withstand as high a load as possible, it is expedient if a spacing of two centre point of the spherical surfaces defining the lateral femur condyle and the medial femur condyle is smaller than the sum of the lateral femur condyle radius of curvature and the medial femur condyle radius of curvature.

In other words, the spherical surfaces defined by the two femur condyles intersect. The larger the femur condyle radii of curvature, the longer the touching lines of the femur part and the meniscus part. The longer these lines are, the smaller the wear of the meniscus part which is preferably formed of a plastics material.

It is advantageous if centre points of lines of intersection between the at least one meniscus joint surface and arbitrary cutting planes containing the rotational axis are located on a cylinder surface that is concentric with the rotational axis. Consequently, they are all at the same distance from the rotational axis. Optionally however, the joint surface recess defined by the meniscus joint surface may vary in depth parallel to the rotational axis. In other words, all the centre points do not necessarily have to lie in one plane. Rathermore, the positions of the centre points can vary in a direction parallel to the rotational axis in dependence on a rotational angle of the respective cutting plane. Thus for example, the joint surface recess can define a minimum spacing between the femur part and the tibia part in the case of a rotational position of 0°, but a larger or even increasing spacing as the deflection increases. In particular, this can help the knee to transfer more or less automatically back into its neutral rotational position.

Expediently, the centre points lie on a centre point plane which runs transversely and in particular perpendicularly to the rotational axis. For example, the centre point plane can run parallel to a tibia surface on which the meniscus part rests. Optionally, the centre point plane could also be inclined to this tibia surface.

The knee joint endoprosthesis can be constructed in a particularly stable manner if the meniscus part is formed in one piece.

Advantageously, the connecting device defines a connecting position in which the tibia part and the femur part are connected to one another inseparably. In this way in particular, a luxation of the knee, i.e. an unintentional detachment of the femur part and the tibia part from each other can be prevented. In the event of such luxation, there is the danger, in particular, that a contact between the femur part and the meniscus part is broken so that they can act on one another in an undefined manner, whereby in particular, the meniscus part can easily be damaged.

It is expedient if the tibia part comprises a meniscus part contact surface pointing in the direction of the meniscus part and if the rotational axis runs transversely and in particular perpendicularly to the meniscus part contact surface. In this way, it is possible, in particular, to transfer forces from the femur part in the direction of a longitudinal axis defined by the lower leg of the patient to the meniscus part and then via this part, to the tibia part. In particular in the case where the tibia part comprises a shaft or is connected to a shaft which can be inserted into a medullary cavity of the tibia, forces can then be diverted from the femur part to the tibia.

Preferably the tibia part and the femur part are mounted such that they are pivotal relative to each other about a hinge axis. The hinge axis makes it possible in particular for a bending movement between the tibia part and the femur part to be permitted in a simple manner so that overall, the knee joint endoprosthesis can simulate a virtually natural bending movement of the knee.

It is expedient if the hinge axis runs transversely of the rotational axis. In particular, it can run perpendicularly to the rotational axis. In addition, the rotational axis can run such as to be displaced with respect to the hinge axis in the anterior direction, for example, through a frontal region of the knee joint endoprosthesis. This arrangement has the advantage, in particular, that the process of implanting the knee joint endoprosthesis is significantly simplified since the tibia part and the femur part can be positioned independently of one another in such a way that the mutually cooperating elements of the connecting device are easily accessible and moveable into engagement with one another.

In accordance with a further preferred embodiment of the invention, provision may be made for the tibia part to comprises a tibia surface on which a meniscus part lower surface of the meniscus part abuts, in particular in a planar manner, and in that the hinge axis runs parallel or substantially parallel to the tibia surface. This arrangement makes it possible, in particular, to optimally divert forces acting on the meniscus part from the femur part into the tibia part. Furthermore, due to the special design of the tibia part, a surgeon can appreciate in a simple and certain manner whether the knee joint endoprosthesis is connected in the desired way to the remaining femur and the remaining part of the tibia during the implantation process.

It is expedient for the rotational axis and the hinge axis to be skewed relative to each other. Thus, in other words, they do not intersect. In particular, this permits the rotational axis to be offset relative to the hinge axis in the anterior direction which simplifies the process of bringing the parts and elements forming the connecting device into engagement during the implantation of the knee joint endoprosthesis.

It is advantageous for the rotational axis to be perpendicular to a plane containing the hinge axis. In particular, this enables a rotation of the femur part and the tibia part about the rotational axis on the one hand whilst making it possible to have a swinging movement about the hinge axis running perpendicularly thereto on the other.

The implantation of the knee joint endoprosthesis is simplified, in particular, in that the connecting device is formed in such a manner that the tibia part and the femur part are connectable to one another after an implantation on the tibia and on the femur. In this way, it is thereby possible in particular to connect the tibia part and the femur part independently of each other to the tibia and the femur of a patient and only to connect them together after appropriate adjustment of the two bones.

A rotation of the tibia part and the femur part relative to each other about the rotational axis is made possible in a simple manner if a rotary bearing element is arranged, formed or held on the tibia part for the purposes of mounting the femur part such as to be rotatable about the rotational axis. For example, the rotary bearing element can be in the form of a rotationally symmetrical pin.

The implantation of the knee joint endoprosthesis can be further simplified in particular in that the rotary bearing element is mounted on the tibia part such as to be rotatable about the rotational axis. Thus for example, the stability of the knee joint endoprosthesis can also be improved in dependence on the design of the rotary bearing element.

It is advantageous if the tibia part comprises a rotary bearing element seating in which the rotary bearing element is held. In this way in particular, a stable connection between the rotary bearing element and the tibia part can be achieved. In particular, the rotary bearing element can be mounted in the rotary bearing element seating of the tibia part such as to be rotatable about the rotational axis.

For the purposes of forming a particularly stable knee joint endoprosthesis, it is expedient for the rotary bearing element to be mounted in the rotary bearing element seating such as to be immovable in a direction parallel to the rotational axis. In this way, it is not possible for the femur part and the tibia part to move away from each other. In particular, a luxation of the knee joint endoprosthesis can thereby be prevented in a simple manner.

Furthermore, it can be expedient if the rotary bearing element is mounted in the rotary bearing element seating such as to be displaceable in a direction parallel to the rotational axis. Such an arrangement is advantageous in particular if a certain degree of movement of the femur part and the tibia part relative to each other parallel to the rotational axis is desirable. In particular, this may actually be necessary if the centre points of the meniscus joint surface radii of curvature do not lie in a plane. In this case, a degree of mobility of the femur part and the tibia part relative to each other parallel to the rotational axis is in fact necessary in order to prevent jamming of the femur part and the meniscus part due to a rotation of the femur part and the tibia part relative to each other.

In accordance with a further preferred embodiment of the invention, provision may be made for the knee joint endoprosthesis to comprise a stop device for limiting a movement of the rotary bearing element and the rotary bearing element seating relative to each other in the distal and/or proximal direction. In particular, a movement of the femur part and the tibia part towards and/or away from each other can be limited with the aid of such a stop device. Thus on the one hand in particular, a means for providing a safeguard against luxation of the knee joint endoprosthesis can be achieved and a load on the meniscus part can be limited on the other.

In order to prevent the rotary bearing element from being able to withdraw from the rotary bearing element seating in an unintentional or unwanted manner, it is expedient if the knee joint endoprosthesis comprises a securing device for securing the rotary bearing element in the rotary bearing element seating.

Preferably, the knee joint endoprosthesis comprises a bearing sleeve for mounting the rotary bearing element, which bearing sleeve defines the rotary bearing element seating. Such a bearing sleeve makes it possible, in particular, to arrange, hold or mount the rotary bearing element in a recess in the tibia part in displaceable manner in order, in particular, to selectively permit or prevent a movement of the parts relative to each other parallel to the rotational axis.

Furthermore, it can be expedient if the tibia part comprises a bearing sleeve seating for accommodating the bearing sleeve. The bearing sleeve seating makes it possible in particular to support the bearing sleeve on the tibia part over a sufficient length parallel to the rotational axis.

Furthermore, it is advantageous if the securing device comprises a securing element for securing the bearing sleeve in the bearing sleeve seating. Such a securing device makes it possible in particular to prevent a luxation of the knee joint endoprosthesis.

Expediently, the stop device comprises a stop which limits a depth of insertion of the bearing sleeve into the bearing sleeve seating. In particular, a minimum spacing between the femur part and the tibia part can thereby be predefined in a simple manner.

It is advantageous if the rotary bearing element seating is closed in the distal direction and open in the proximal direction. On the one hand, the rotary bearing element seating can thereby form a stop in order to limit a movement of the femur part and the tibia part towards one another. On the other hand, due to the open arrangement in the proximal direction, it is possible for the rotary bearing element to project out of the rotary bearing element seating and in particular too, to protrude beyond the tibia surface described above in order to be brought directly into engagement with the femur part or with a connecting element that is articulated thereto and is pivotal about the hinge axis.

In order to improve the stability of the knee joint endoprosthesis, it is expedient, in particular, if the rotary bearing element seating extends at least partly above and/or below the tibia surface.

In order to prevent metallic parts from striking together, it is expedient for the meniscus part to be made entirely or partly of a plastics material.

In particular it is advantageous if the plastics material is or comprises polyethylene (PE), polyethylene of ultrahigh molecular weight (UHMWPE) or polyetheretherketone. Such plastics materials in particular are certified as permissible implant materials and exhibit a desired abrasion resistance in dependence on the way in which they are produced in order to minimize wear of the knee joint endoprosthesis.

Figure 1:
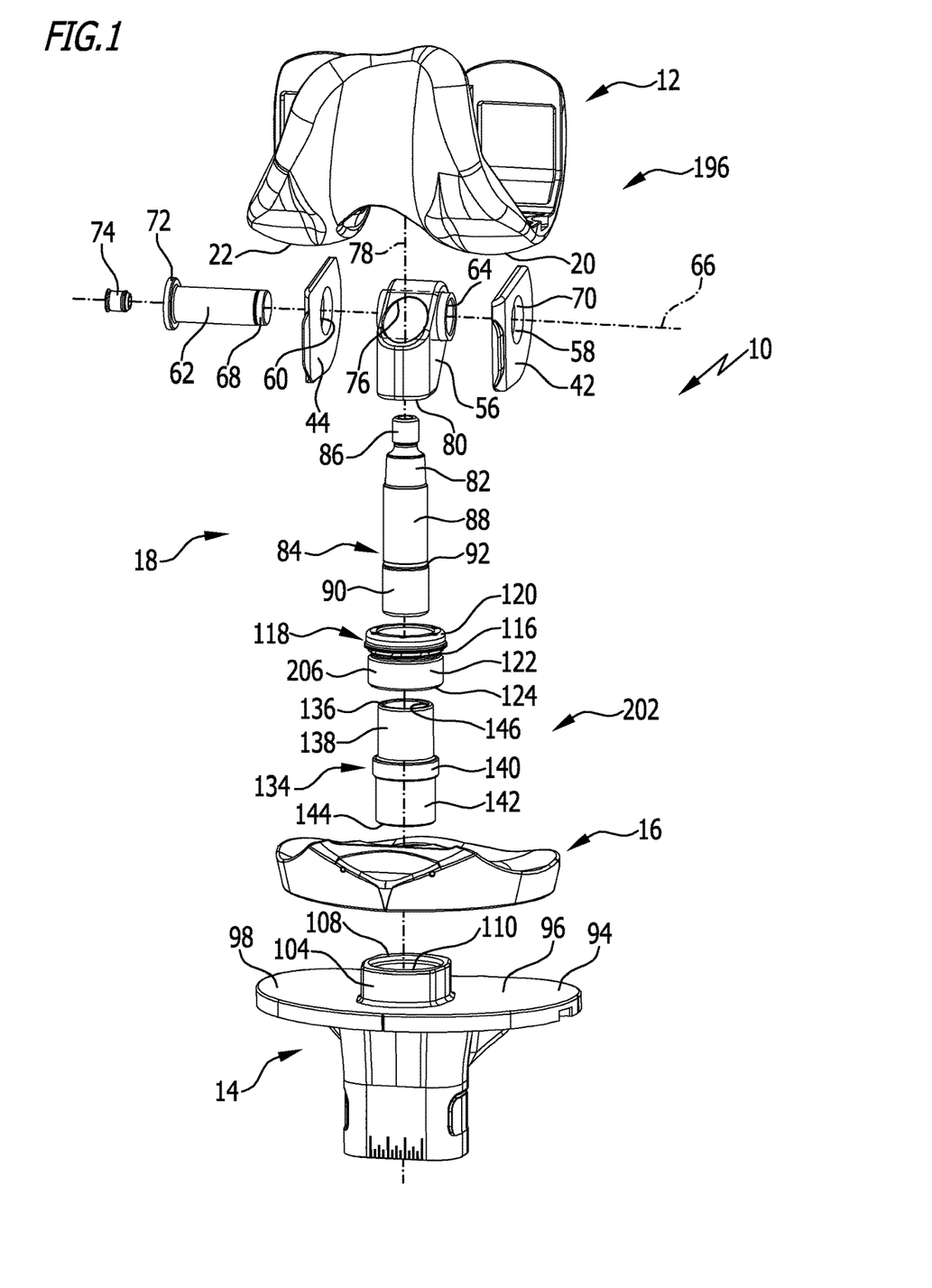
FIG. 1: shows a schematic perspective exploded illustration of an exemplary embodiment of a knee joint endoprosthesis.

A knee joint endoprosthesis together with the individual parts thereof is illustrated exemplarily in FIG. 1 and is designated overall by the reference symbol 10. It comprises a femur part 12 which can be fixed to a femur of a patient with or without a shaft, a tibia part 14 which can be fixed to a tibia of a patient and a meniscus part 16 which is arranged on the tibia part 14 in at least mutually non-rotatable manner between the femur part 12 and the tibia part 14. Furthermore, the knee joint endoprosthesis 10 comprises a connecting device 18 comprising a plurality of parts with which the femur part 12 and the tibia part 14 can be connected to one another.

The femur part 12 comprises a medial femur condyle 20 and a lateral femur condyle 22. These form joint surfaces of the femur part 12, namely, a medial femur condyle surface 24 and a lateral femur condyle surface 26.

Both the medial femur condyle surface 24 and the lateral femur condyle surface 26 form a section of a respective spherical surface 28 and 30 which define ball centre points 32 and 34. A medial femur condyle radius of curvature 36 of the medial femur condyle surface 24 corresponds to a lateral femur condyle radius of curvature 38 of the lateral femur condyle surface 26 in the exemplary embodiment illustrated in the Figures. A spacing 40 of the ball centre points 32 and 24 is smaller than the sum of the medial femur condyle radius of curvature 36 and the lateral femur condyle radius of curvature 38.

A recess 46 bounded by mutually parallel side walls 42 and 44 is formed between the two femur condyles 20 and 22. This is closed at the rear by a cover wall 48.

The cover wall 48 comprises an opening 50 which directly adjoins a somewhat narrower slot 52. The slot 52 extends substantially in the anterior posterior direction. The side walls 42 and 44 together with the cover wall 48 form a joint box 54 for a pivot pin 56.

The side walls 42 and 44 each comprise a respective opening 58 and 60 into which a joint shaft 62 is inserted. The pivot pin 56 has a transverse boring 64 which extends along a longitudinal axis that is defined thereby, wherein said boring defines a hinge axis 66 and serves for accommodating the joint shaft 62. The joint shaft 62 can be provided at one end thereof with a short externally threaded section 68 which corresponds to an internal thread 70 that is formed in the opening 58 of the side wall 42. Thus overall a hinge joint 196 is formed between the femur part 12 and the pivot pin 56.

The other end of the joint shaft 62 comprises a ring flange 72 which extends away from the hinge axis 66 in a radial direction and positively engages in the recess formed in the side wall 44. Furthermore, the end of the joint shaft 62 provided with the ring flange 72 comprises a tool element seating which is in the form of a multilobular internal driving feature for example, and is closed by an appropriate closure plug 74.

The pivot pin 56 is mounted in the recess 46 such as to be pivotal about the hinge axis 66 in the manner described. The hinge axis 66 runs parallel or substantially parallel to a connecting line of the ball centre points 32 and 34.

Furthermore, a longitudinal opening 76 which runs in the anterior direction with reference to the transverse boring 64 is formed in the pivot pin 56. This opening defines a rotational axis 78 of the knee joint endoprosthesis 10.

Commencing from an end 80 pointing in the direction of the meniscus part 16, the longitudinal opening 76 is in the form of an inner cone which corresponds to a conical section 82 of a rotationally symmetrical rotary bearing element 84.

Adjoining the conical section 82 of the rotary bearing element 84 at one side, there is an externally threaded section 86 of somewhat reduced external diameter onto which a locknut that is not illustrated in the Figures can be screwed in order to ensure a preferably self-locking cone-clamping action between the rotary bearing element 84 and the pivot pin 56. Ideally, the externally threaded section 86 is dimensioned such that it does not protrude from the longitudinal opening 76.

At the diametrically thicker end thereof, the conical section 82 is adjoined by a cylinder section 88 which is about three times longer. In the direction of the tibia part 14, there is a further cylinder section 90 which forms one end of the rotary bearing element 84. The cylinder section 90 is of somewhat greater external diameter than the cylinder section 88 so that a an annular stop surface 92 of a stop device 200 pointing in the direction of the femur part 12 is formed for limiting movement of the rotary bearing element 84 parallel to the rotational axis 78.

The tibia part 14 comprises a plate 94 having an upper surface 96 facing in the direction of the femur part 12 which defines a flat tibia surface 98. At a lower surface 100 of the plate 94, there is formed a short shaft support 102 which can optionally be lengthened in a modular manner with a shaft that is not illustrated in the Figures.

A short, sleeve-shaped support 104 extends from the tibia surface 98 in the direction of the femur part 12. This support has a non-round outer contour 106 as can be easily perceived in particular, in FIG. 7.

Commencing from an end 108 pointing in the direction of the femur part 12, there is formed in the tibia part 14 a blind hole 110 which is concentric with the rotational axis 78 and comprises a base 112 facing in the direction of the femur part 12. In the interior of the blind hole 110 in the region of the support 104, there is formed a short internally threaded section 114 which corresponds to an externally threaded section 116 of a locking sleeve 118.

The locking sleeve 118 has an annular flanged end 120 having an external diameter that is dimensioned such as to form a stop which strikes the end 108 of the support 104 when the locking sleeve 118 is screwed into the support 104. The length of the locking sleeve 118 is only marginally greater than the height of the support 104 rising up from the tibia surface 98.

Adjoining the externally threaded section 116, there is a short cylindrical sleeve section 122 having an external diameter which is matched to an internal diameter of the blind hole 110 within the region of the support 104.

When the locking sleeve 118 is screwed into the blind hole 110, the end thereof 124 directed away from the femur part 12 reaches approximately up to an annular recess 126 of the blind hole 110. The internal diameter of the blind hole 110 is somewhat reduced in the region of the recess 126 so that a short hollow-cylindrical wall section 128 is defined. A further recess 130 follows the wall section 128 and the internal diameter of the blind hole 110 is again reduced in the region thereof. The blind hole 110 is in the form of a hollow-cylindrical opening 132 in the direction of the base 112.

Furthermore, for the purposes of securely connecting the femur part 12 and the tibia part 14, the connecting device 18 comprises a bearing sleeve 134 which is rotationally symmetrical with respect to the rotational axis 78. Commencing from an end 136 oriented in the direction of the femur part 12, this bearing sleeve comprises a first sleeve section 138 to which a short second sleeve section 140 of greater external diameter is adjoined. In turn, there is adjoined thereto a third sleeve section 142 which extends up to the other end 144 of the bearing sleeve 134. The external diameter of the third sleeve section 142 is somewhat greater than an external diameter of the first sleeve section 138, but is somewhat smaller than an external diameter of the second sleeve section 140.

In the interior thereof, the bearing sleeve 134 comprises a rotationally symmetrical longitudinal opening 146 which, in the region of the second sleeve section 140, has an internal diameter that widens in the form of a single-step in the direction of the end 144 and defines a rotary bearing element seating 198.

Figure 2:
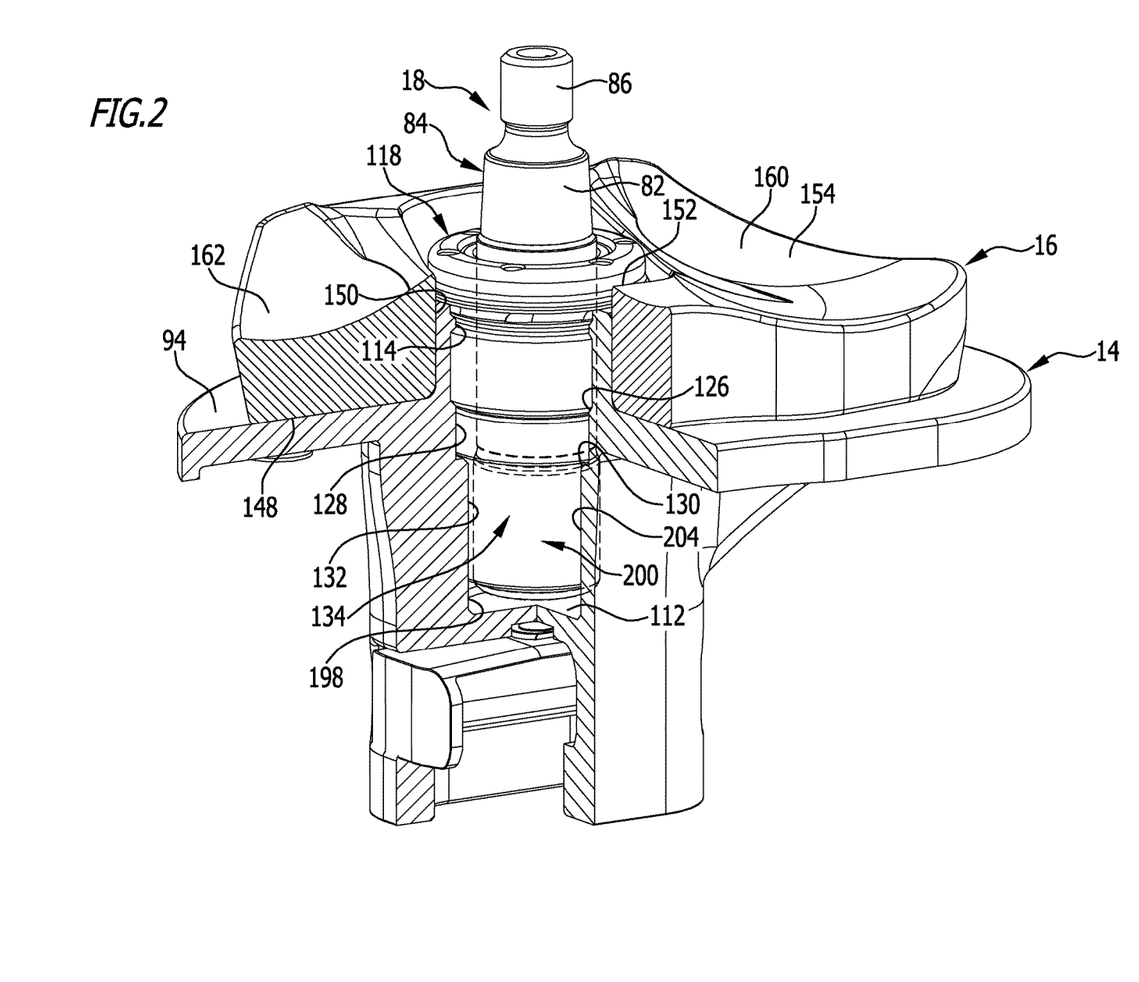
FIG. 2: a partly sectional perspective view of the meniscus part of the knee joint endoprosthesis depicted in FIG. 1 fixed to the tibia part.
Figure 3:
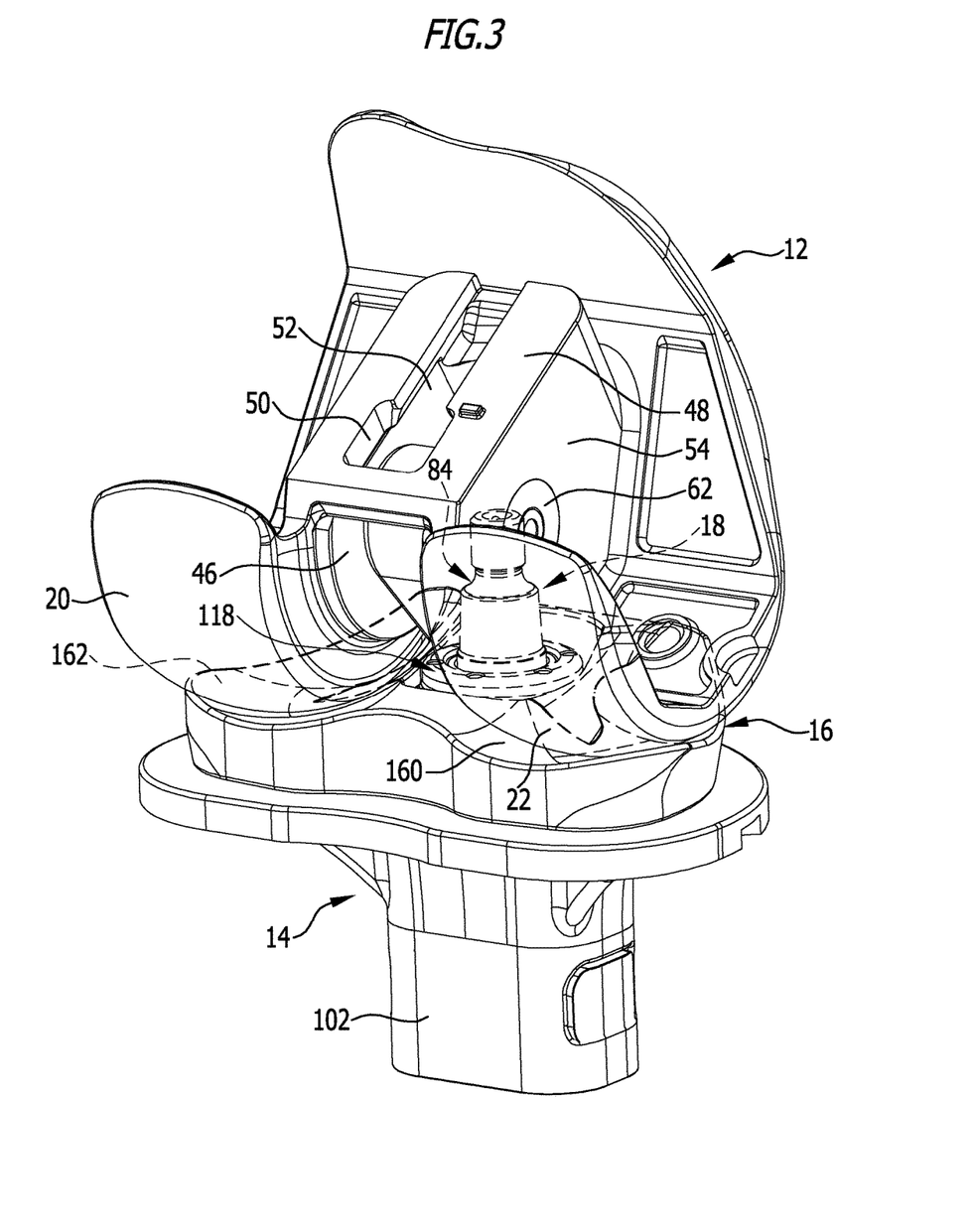
FIG. 3: a schematic, partly cut-away overall view of the assembled knee joint endoprosthesis depicted in FIG. 1 incorporating the femur part, the meniscus part and the tibia part as seen from the posterior direction.
Figure 4:
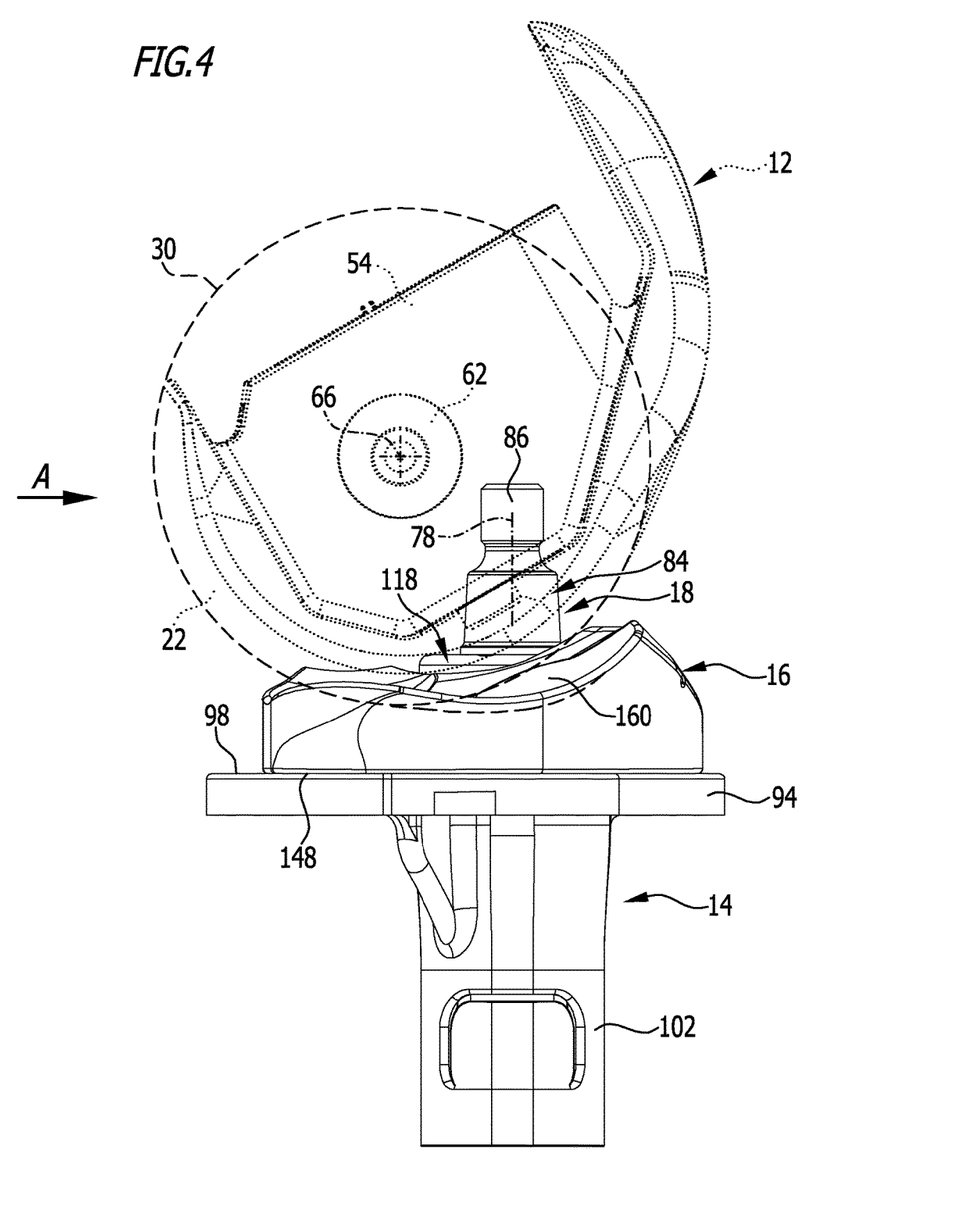
FIG. 4: a partly cut-away side view of the knee joint endoprosthesis depicted in FIG. 1.
Figure 5:
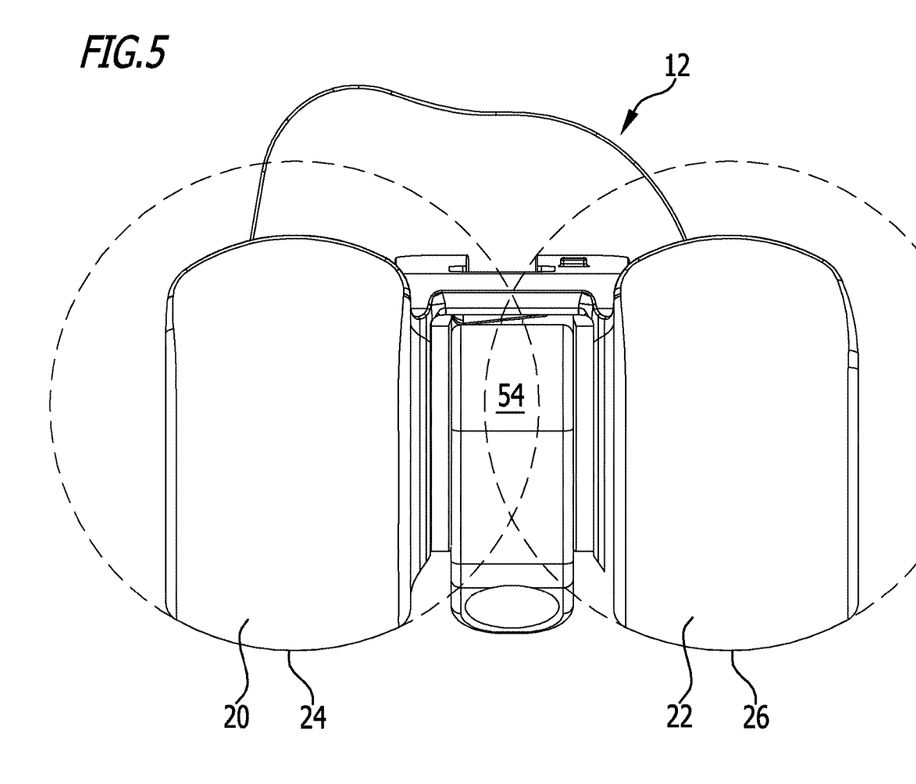
FIG. 5: a plan view of the femur part from the posterior in a stretched position of the knee joint endoprosthesis depicted in FIG. 1.
Figure 6:
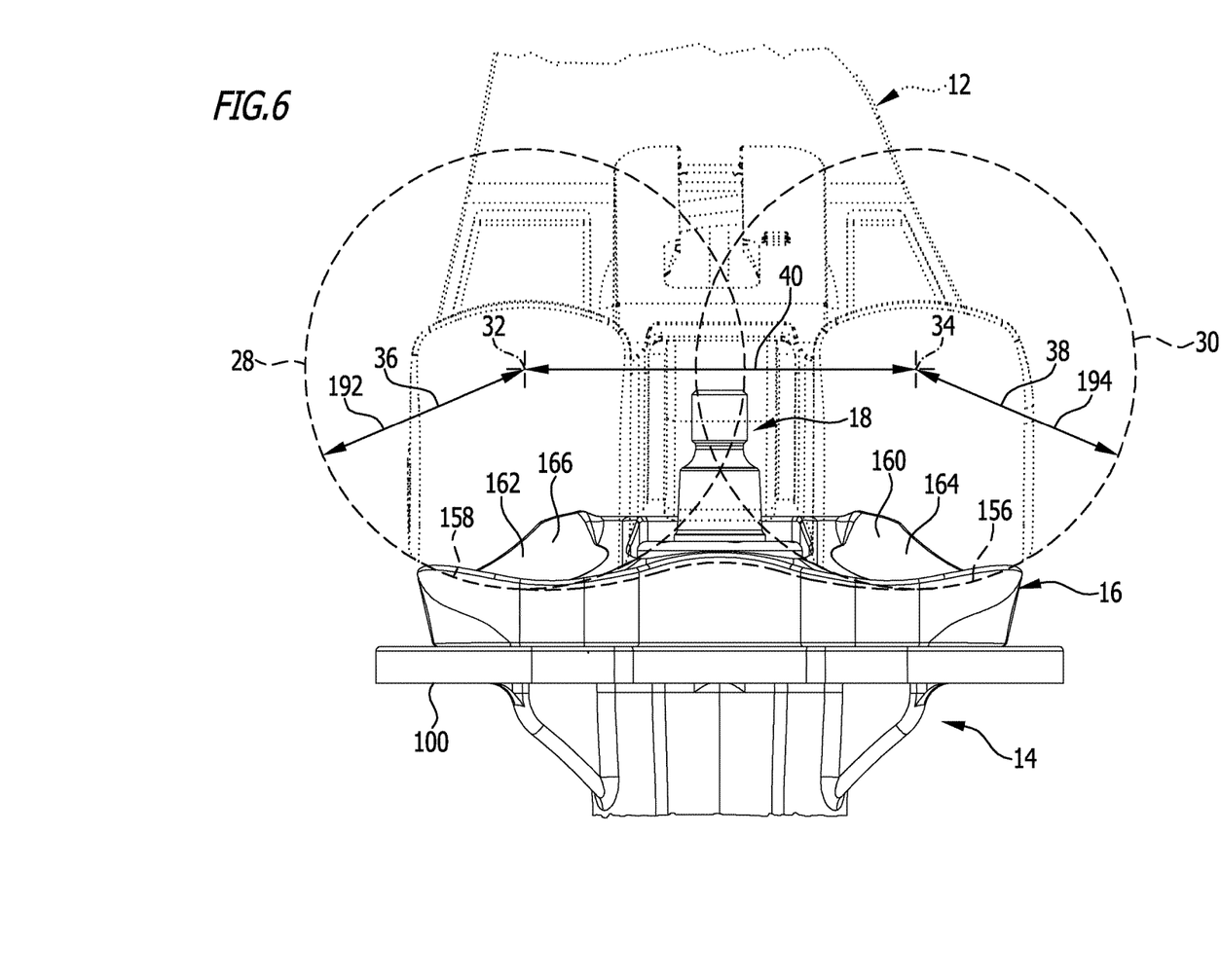
FIG. 6: a partly cut-away view of the knee joint endoprosthesis depicted in FIG. 1 from the posterior, i.e. in the direction of the arrow A in FIG. 4 and in the direction of the arrow B in FIG. 7.

The meniscus part 16 comprises a meniscus part lower surface 148 which is flat and rests in planar manner against the tibia surface 98 defining a meniscus part contact surface. Furthermore, the meniscus part 16 is provided with an opening 150 having an internal contour 152 which is matched to the outer contour 106 of the support 104. In this way, the meniscus part 16 can be placed on the tibia part 14 from above and, due to the non-round shape and the outer contour 106 as well as the correspondingly formed internal contour 152, it is prevented from rotation on the tibia part 14, i.e. is fixed in mutually non-rotatable manner.

An upper surface 154 of the meniscus part 16 comprises a medial meniscus joint surface 156 and a lateral meniscus joint surface 158. The meniscus joint surfaces 156 and 158 are matched to the femur condyle surfaces 24 and 26 and have medial and lateral meniscus joint surface radii of curvature 192 and 194 which preferably correspond to the femur condyle radii of curvature 36 and 38.

The meniscus joint surfaces 156 and 158 define medial and lateral joint surface recesses 160 and 162 which are in the form of short curved hollows 164 and 166 that are spatially separated from one another. Each of the two hollows 164 and 166 serves for mounting and guiding one of the two femur condyles 20 and 22.

The hollows 164 and 166 are convexly curved with respect to the rotational axis 78 in a direction pointing away therefrom and run concentrically thereabout. In a section including cutting planes 168 and 170 containing the rotational axis, the hollows 164 and 166 define sections of a circular arc having radii 172 and 174 which correspond to the femur condyle radii of curvature 36 and 38 respectively. The hollows 164 and 166 are thus in the form of hollow-cylindrical sections on the upper surface 154 of the meniscus part 16 which run concentrically with respect to the rotational axis 78. Centre points of the sections of a circular arc defined by the hollows 164 and 166 including the cutting planes 168 and 170 coincide with the ball centre points 32 and 34 of the femur condyles 20 and 22 when the femur condyle surfaces 24 and 26 of the femur part 12 rest on the meniscus joint surfaces 156 and 158.

Figure 7:
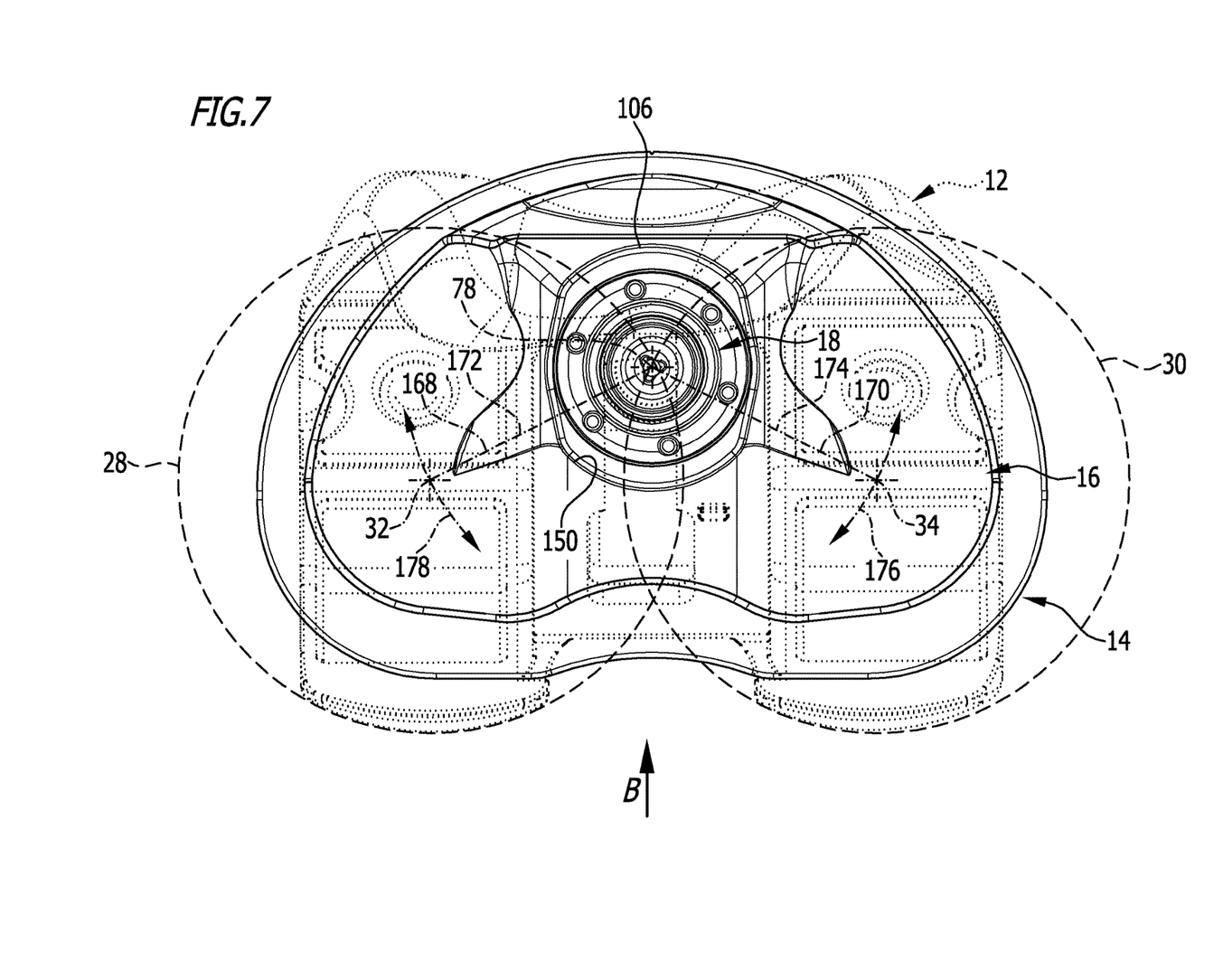
FIG. 7: a partly cut-away view of the knee joint endoprosthesis depicted in FIG. 1 in a plan view of the meniscus part in the stretched position.

The hollows 164 and 166 are not flat but have at least one local minimum, namely, in such a way that planes of symmetry of the two femur condyles 20 and 22 on the one hand as well as the tibia part 14 on the other are aligned in parallel with each other, and optionally, coincide with one another, when the femur condyles 20 and 22 are respectively located in the local minimum of the hollows 164 and 166. Starting from this basic position which is schematically illustrated in FIG. 7, the femur part 12 can now be twisted in the direction of the arrows 176 and 178 relative to the meniscus part 16 and thus too relative to the tibia part 14 in the medial or lateral direction about the rotational axis 78 or be rotated within a restricted angular range when the knee joint endoprosthesis 10 is mounted in position.

Commencing from the basic position, the spacing of the meniscus joint surfaces 156 and 158 and that of the femur condyle surfaces 24 and 26 from the meniscus part lower surface 148 preferably increases in the medial and lateral direction so that, as a result of a corresponding rotation of the femur part 12 and the tibia part 14 relative to each other, the femur part 12 is distanced somewhat from the tibia part 14.

Figure 8:
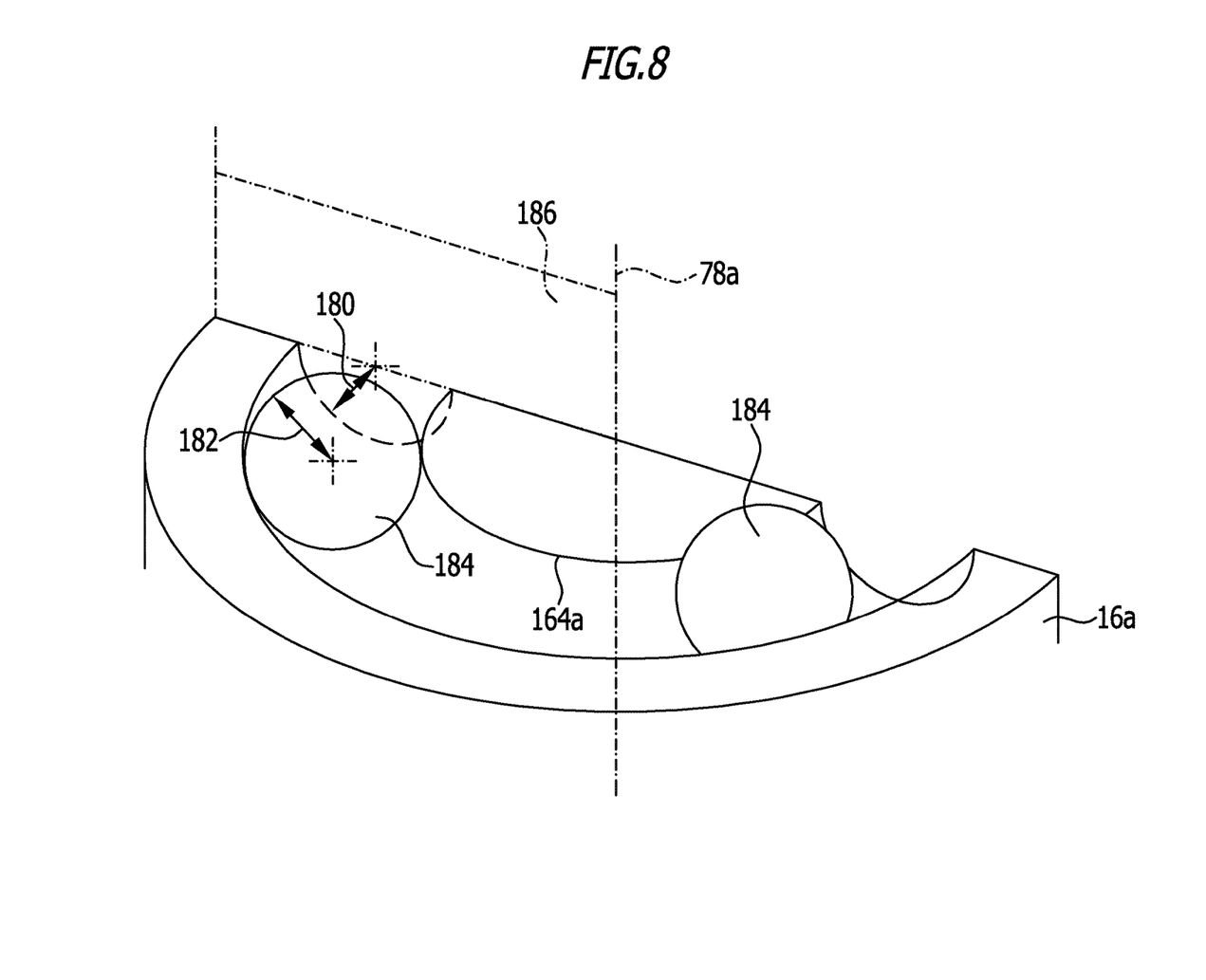
FIG. 8: a schematic view of two balls guided in a hollow formed concentrically with a longitudinal axis.

The cooperation between the femur condyles 20 and 22 and the meniscus joint surfaces 156 and 168 of the meniscus part 16 is illustrated schematically in FIG. 8. The meniscus part 16a illustrated schematically in FIG. 8 comprises a hollow 164a which is in the form of a hollow-cylindrical recess and forms a joint surface recess 160a of the meniscus part 16a.

An internal radius 180 of the hollow 164a corresponds to a radius 182 of the two balls 184 guided in the hollow 164a which represent femur condyles in this schematic illustration. If the internal radius 180 and the radius 182 are identical, this results in a linear contact along a section of a circular arc which is defined by a line of intersection between a cutting plane 186 containing the rotational axis 78a and the meniscus part 16a.

Due to the concentric alignment of the hollow 164a relative to the rotational axis 78a, both balls 184 are guided optimally and enable an optimal contact to be obtained, thus in particular, a maximized contact area or contact line between the balls 184 and the hollow 164a of the meniscus part 16a.

The cooperation between the femur condyles 20 and 22 and the meniscus joint surfaces 156 and 158 corresponds to the cooperation between the balls 184 and the hollow 164a. In this way, it is possible to produce a knee joint endoprosthesis 10 which comprises both a hinge joint and also enables a rotation of the femur part 12 and the tibia part 14 about the rotational axis 78, and this in the case of a meniscus part 16 arranged on the tibia part 14 in mutually non-rotatable manner.

For the implantation of the knee joint endoprosthesis 10, one proceeds as follows.

Firstly, the femur part 12 and the tibia part 14 are fixed to the appropriately prepared femur and tibia of the patient. Hereby, the femur part 12 is already coupled in articulated manner to the pivot pin 56 of the connecting device 18 in the way described above.

In a next step, the meniscus part 16 can be placed on the tibia part 14.

For the purpose of connecting the femur part 12 and the tibia part 14 to one another, the cylinder section 90 of the rotary bearing element 84 is then inserted forwardly into the blind hole 110. The bearing sleeve 134 with the end 144 thereof in front is thereafter pushed over the rotary bearing element 84 and inserted into the blind hole 110, namely, until the second sleeve section 140 strikes the recess 130.

Next, the locking sleeve 118, which forms a securing element 206 of a securing device 202 for securing the rotary bearing element 84 in the blind hole 100 defining a bearing sleeve seating 204, is inserted with the end 124 thereof in front into the support 104 and screwed thereto. The end 124 of the locking sleeve 118 then abuts against the second sleeve section 140 and prevents it from movement in the axial direction.

The rotary bearing element 84 is moveable somewhat in the axial direction. The maximum degree of movement thereof is limited by the stop device 200. This comprises the base 112 serving as a stop. In particular, the maximum degree of movement is defined by the spacing between the base 112 and the recess 130 in the interior of the bearing sleeve 134 which serves as a further stop of the stop device 200 for the cylinder section 90. The rotary bearing element 84 can thus strike the base 112 on the one hand and restrict movement of the femur part 12 in the direction of the tibia part 14, whilst on the other hand, the stop surface 92 can strike the recess in the interior of the bearing sleeve 134 and limit a movement of the femur part 12 away from the tibia part 14.

When the rotary bearing element 84 is secured to the tibia part 14 in the manner described, the rotary bearing element 84 can be inserted, with the externally threaded section 86 thereof in front, through the end 80 of the longitudinal opening 76 in the pivot pin 56. The pivot pin 56 and the rotary bearing element 84 are connected firmly to one another by a self-locking conical clamping effect between the conical section 82 and the corresponding inner cone section in the pivot pin 56. As described, for the purposes of securing the conical clamping effect, a locknut can optionally be screwed onto the externally threaded section 86.

The described knee joint endoprosthesis 10 forms a so-called "rotating hinge" knee with a fixed meniscus part 16 because the meniscus part 16 cannot be twisted relative to the tibia part 14 as previously explained.

The connecting device 18 forms a luxation safe-guarding arrangement which prevents the femur condyles 20 and 22 of the femur part 12 from being able to jump out of the meniscus joint surfaces 156 and 158 of the meniscus part 16.

Due to the special formation of the femur condyles 20 and 22 and the corresponding meniscus joint surfaces 156 and 158, wear and tear can be minimized despite the possibility for the femur part 12 and the tibia part 14 to rotate relative to each other about the rotational axis 78.

In the exemplary embodiment illustrated in FIGS. 1 to 7, the varying depth of the hollow 164 or 166 with respect to the meniscus part lower surface 148 additionally increases a ligament tension in the event of a deflection of the femur part 12 relative to the tibia part 14 about the rotational axis 78 so that even in the case of a rotation, for example in an angular range of +−20° and in particular +−12° about the rotational axis 78, an additional stabilization of the implanted knee occurs if the ligament system of the patient comprising a part of the lateral ligaments of the knee still remains.

The knee joint endoprosthesis 10 is preferably made of a body-compatible metal up to the meniscus part 16. It can be partly formed from an implant steel or else from titanium or a titanium alloy. In particular, the meniscus part 16 can be formed of polyethylene and in particular of high-molecular-weight polyethylene (UHMWPE).

LIST OF REFERENCE SYMBOL 10 knee joint endoprosthesis
12 femur part 14 tibia part
16 meniscus part
18 connecting device
20 medial femur condyle
22 lateral femur condyle
24 medial femur condyle surface
26 lateral femur condyle surface
28 spherical surface
30 spherical surface
32 ball centre point
34 ball centre point
36 medial femur condyle radius of curvature
38 lateral femur condyle radius of curvature
40 spacing
42 side wall
44 side wall
46 recess
48 cover wall
50 opening
52 slot
54 joint box
56 pivot pin
58 opening
60 opening
62 joint shaft
64 transverse boring
66 hinge axis
68 externally threaded section
70 internal thread
72 ring flange
74 plug
76 longitudinal opening
78 rotational axis
80 end
82 conical section
84 rotary bearing element
86 externally threaded section
88 cylinder section
90 cylinder section
92 stop surface
94 plate
96 upper surface
98 tibia surface
100 lower surface
102 shaft support
104 support
106 outer contour
108 end
110 blind hole
112 base
114 internally threaded section
116 externally threaded section
118 locking sleeve
120 end
122 sleeve section
124 end
126 recess
128 wall section
130 recess
132 opening
134 bearing sleeve
136 end
138 first sleeve section
140 second sleeve section
142 third sleeve section
144 end
146 longitudinal opening
148 meniscus part lower surface
150 opening
152 internal contour
154 upper surface
156 medial meniscus joint surface
158 lateral meniscus joint surface
160 medial joint surface recess
162 lateral joint surface recess
164 hollow
166 hollow
168 cutting plane
170 cutting plane
172 radius
174 radius
176 arrow
178 arrow
180 internal radius
182 radius
184 ball
186 cutting plane
192 medial meniscus joint surface radius of curvature
194 lateral meniscus joint surface radius of curvature
196 hinge joint
198 rotary bearing element seating
200 stop device
202 securing device
204 bearing sleeve seating
206 securing element

What is claimed is:

1. Knee joint endoprosthesis, comprising:
a tibia part,
a femur part,
a meniscus part permanently fixed against rotation on the tibia part in an implanted state of the knee joint endoprosthesis, and
a connecting device for connecting the tibia part to the femur part in an articulated manner,
the femur part comprising at least one femur condyle having a femur condyle surface,
the tibia part comprising a support for the meniscus part extending from a tibia surface, the support comprising a non-round outer contour,
the meniscus part comprising:
at least one upper surface which faces the femur part and at least one meniscus joint surface which touches the femur condyle surface of the at least one femur condyle, and
an opening comprising a non-round inner contour conforming to the non-round outer contour of the support, and
wherein:
in the implanted state, the support is received in the opening of the meniscus part, fixing the meniscus part and the tibia part together and preventing rotation of the meniscus part relative to the tibia part,
the femur part and the tibia part are mounted such as to be rotatable relative to each other about a rotational axis,
the femur condyle surface of the at least one femur condyle and the at least one meniscus joint surface are formed in correspondence with one another in such a manner that the femur condyle surface of the at least one femur condyle defines a section of a spherical surface, and
the at least one meniscus joint surface is formed as a joint surface recess in the form of a curved hollow which is matched to the femur condyle surface.

2. A knee joint endoprosthesis in accordance with claim 1, wherein:
the at least one femur condyle comprises a medial femur condyle and a lateral femur condyle which respectively define a medial femur condyle surface and a lateral femur condyle surface,
the at least one meniscus joint surface comprises a medial meniscus joint surface and a lateral meniscus joint surface, and
the medial femur condyle surface touches the medial meniscus joint surface and the lateral femur condyle surface touches the lateral meniscus joint surface.

3. A knee joint endoprosthesis in accordance with claim 2, wherein one of:
the medial femur condyle surface and the lateral femur condyle surface have an identical femur condyle radius of curvature, or
the medial femur condyle surface and the lateral femur condyle surface have femur condyle radii of curvature which differ from each other.

4. A knee joint endoprosthesis in accordance with claim 2, wherein one of:
the medial meniscus joint surface and the lateral meniscus joint surface have an identical meniscus joint surface radius of curvature, or
the medial meniscus joint surface and the lateral meniscus joint surface have meniscus joint surface radii of curvature which differ from each other.

5. A knee joint endoprosthesis in accordance with claim 1, wherein the at least one meniscus joint surface is formed concentrically with respect to the rotational axis.

6. A knee joint endoprosthesis in accordance with claim 1, wherein the at least one meniscus joint surface is concavely curved and has a meniscus joint surface radius of curvature in a cutting plane containing the rotational axis which corresponds to a femur condyle radius of curvature of the femur condyle surface of the at least one femur condyle which is convexly curved.

7. A knee joint endoprosthesis in accordance with claim 6, wherein
the at least one femur condyle comprises a medial femur condyle and a lateral femur condyle which respectively define a medial femur condyle surface and a lateral femur condyle surface,
the at least one meniscus joint surface comprises a medial meniscus joint surface and a lateral meniscus joint surface, and
at least one of:
A) the meniscus joint surface radii of curvature of the medial meniscus joint surface and the lateral meniscus joint surface in cutting planes containing the rotational axis are identical,
and
B) a spacing of two center points of the spherical surfaces defining the lateral femur condyle and the medial femur condyle is smaller than a sum of the lateral femur condyle radius of curvature and the medial femur condyle radius of curvature.

8. A knee joint endoprosthesis in accordance with claim 1, wherein:
center points of lines of intersection between the at least one meniscus joint surface and cutting planes containing the rotational axis are located on a cylinder surface that is concentric with the rotational axis, and
the center points lie on a center point plane which runs transversely to the rotational axis.

9. A knee joint endoprosthesis in accordance with claim 1, wherein at least one of:
A) the meniscus part is formed in one piece,
B) the connecting device defines a connecting position in which the tibia part and the femur part are connected to one another inseparably,
and
C) the tibia part comprises a meniscus part contact surface pointing in a direction of the meniscus part and the rotational axis runs transversely to the meniscus part contact surface.

10. A knee joint endoprosthesis in accordance with claim 1, wherein the tibia part and the femur part are mounted such that they are pivotal relative to each other about a hinge axis.

11. A knee joint endoprosthesis in accordance with claim 10, wherein:
the hinge axis runs transversely to the rotational axis,
the tibia part comprises a tibia surface on which a meniscus part lower surface of the meniscus part rests, and
the hinge axis runs parallel or substantially parallel to the tibia surface.

12. A knee joint endoprosthesis in accordance with claim 10, wherein at least one of:
A) the rotational axis and the hinge axis are skewed relative to each other,
B) the rotational axis is perpendicular to a plane containing the hinge axis,
and
C) the connecting device is formed in such a manner that the tibia part and the femur part are connectable to one another after an implantation on the tibia and on the femur.

13. A knee joint endoprosthesis in accordance with claim 1, wherein a rotary bearing element is arranged, formed or held on the tibia part for mounting the femur part so as to be rotatable about the rotational axis.

14. A knee joint endoprosthesis in accordance with claim 13, wherein at least one of:
A) the rotary bearing element is mounted on the tibia part such as to be rotatable about the rotational axis,
and
B) the tibia part comprises a rotary bearing element seating in which the rotary bearing element is held.

15. A knee joint endoprosthesis in accordance with claim 14, wherein the tibia part comprises the rotary bearing element seating in which the rotary bearing element is held, and one of:
A) the rotary bearing element is mounted in the rotary bearing element seating such as to be immovable in a direction parallel to the rotational axis,
or
B) the rotary bearing element is mounted in the rotary bearing element seating such as to be displaceable in a direction parallel to the rotational axis.

16. A knee joint endoprosthesis in accordance with claim 14, wherein the tibia part comprises the rotary bearing element seating in which the rotary bearing element is held, further comprising at least one of:
A) a stop device for limiting a movement of the rotary bearing element and the rotary bearing element seating relative to each other in at least one of a distal direction and a proximal direction,
B) a securing device for securing the rotary bearing element in the rotary bearing element seating,
and C) a bearing sleeve which defines the rotary bearing element seating for mounting the rotary bearing element.

17. A knee joint endoprosthesis in accordance with claim 16, further comprising the bearing sleeve which defines the rotary bearing element seating for mounting the rotary bearing element, wherein the tibia part comprises a bearing sleeve seating for accommodating the bearing sleeve.

18. A knee joint endoprosthesis in accordance with claim 17, wherein at least one of:
A) the knee joint endoprosthesis further comprises the securing device for securing the rotary bearing element in the rotary bearing element seating, wherein the securing device comprises a securing element for securing the bearing sleeve in the bearing sleeve seating,
and
B) the knee joint endoprosthesis further comprises the stop device for limiting the movement of the rotary bearing element and the rotary bearing element seating relative to each other in at least one of the distal direction and the proximal direction, wherein the stop device comprises a stop which limits a depth of insertion of the bearing sleeve into the bearing sleeve seating.

19. A knee joint endoprosthesis in accordance with claim 14, wherein the tibia part comprises the rotary bearing element seating in which the rotary bearing element is held, and at least one of:
A) the rotary bearing element seating is closed in a distal direction and open in a proximal direction,
and
B) the rotary bearing element seating extends at least partly above and/or below the tibia surface.

20. A knee joint endoprosthesis in accordance with claim 1, wherein:
the meniscus part is made entirely or partly of a plastics material,
the plastics material comprises a polyethylene (PE) material of an ultrahigh molecular weight (UHMWPE) or a polyetheretherketone material.

* * * * *